US006656893B2

(12) United States Patent
Saito et al.

(10) Patent No.: US 6,656,893 B2

(45) Date of Patent: Dec. 2, 2003

(54) TRANSPARENT BAR SOAP COMPOSITION COMPRISING GLYCERINE DERIVATIVE

(75) Inventors: Yoshinobu Saito, Ibaraki (JP); Daiji Nagahama, Takatsuki (JP); Nobuyuki Kishi, Settsu (JP); Tetsuo Nishina, Takatsuki (JP)

(73) Assignees: Shiseido Honecake Industry Co., Ltd., Osaka (JP); P & PF Co., Ltd., Osaka (JP)

(*) Notice: Subject to any disclaimer, the term of this patent is extended or adjusted under 35 U.S.C. 154(b) by 141 days.

(21) Appl. No.: 10/006,647

(22) Filed: Dec. 10, 2001

(65) Prior Publication Data

US 2002/0132743 A1 Sep. 19, 2002

(30) Foreign Application Priority Data

Dec. 25, 2000 (JP) ....................................... 2000-392137
Sep. 17, 2001 (JP) ....................................... 2001-280961

(51) Int. Cl.[7] .................................................. A61K 7/50

(52) U.S. Cl. ....................... 510/141; 510/147; 510/152; 510/421; 510/481

(58) Field of Search ................................ 510/141, 147, 510/152, 421, 481

(56) References Cited

U.S. PATENT DOCUMENTS 5,154,849 A * 10/1992 Visscher et al. ....... 252/174.15
5,496,489 A 3/1996 Dussault et al.

FOREIGN PATENT DOCUMENTS

EP 0 294 010 A1 12/1988
EP 0 426 984 A2 5/1991
JP 63-275700 A 11/1988
JP 11-106307 A 4/1999
JP 11-124598 A 5/1999

OTHER PUBLICATIONS

Kim Myong Kon; Abstract for KR 9 511 401 B; Oct. 2, 1995.

* cited by examiner

*Primary Examiner*—Necholus Ogden
(74) *Attorney, Agent, or Firm*—Birch, Stewart, Kolasch & Birch, LLP

(57) ABSTRACT

The present invention relates to a transparent bar soap composition comprising a sodium salt of a fatty acid or a mixed sodium/potassium salt of a fatty acid, at least one amphoteric surfactant selected from the group consisting of compounds represented by formulas (A) to (C), a nonionic surfactant, and at least one glycerin derivative.

(A)

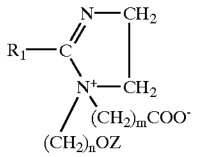

(B)

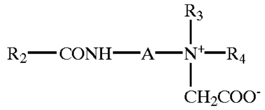

(C)

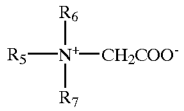

4 Claims, 1 Drawing Sheet

TRANSPARENT BAR SOAP COMPOSITION COMPRISING GLYCERINE DERIVATIVE

FIELD OF THE INVENTION

The present invention relates to a transparent bar soap composition which is obtainable without the aging process after forming.

BACKGROUND OF THE INVENTION

To manufacture a transparent bar soap by a framing method, the following ingredients and process have been traditionally utilized. Namely, fatty acids or fats/oils are dissolved in a lower alcohol such as ethanol. In the next-step, sodium hydroxide was added for neutralization or saponification. Then, humectants like sugar, sorbitol and glycerin are blended and dissolved therein. Where necessary, colorants, fragrances, medicinal ingredients, plant extracts, etc. are added and dissolved as well. This mixture is poured into a given frame, cooled to solidify, and then cut into a certain form. The formed products are aged in order to let volatile components evaporate, until the weight of these products is reduced to a predetermined degree. Finally, the aged products are re-shaped and packaged for commercial distribution.

In this traditional soap-making method, the aging process imparts some advantages to the formed product. For example, the formed product acquires appropriate hardness through the aging process. Besides, the aged product shows a remarkable storage stability, because it does not sweat (i.e. no liquid appears on its surface like sweat) even when stored under severe conditions of high temperature and high humidity. In addition, as for a half-used product, the surface is less likely to turn cloudy.

Nevertheless, the conventional soap-making method requires an extensive aging period which depends on the weight of a formed product. For example, a 100-gram product needs an aging period of as long as about 60 days. In addition, the products to be aged occupy a vast space. Under these circumstances, the time-consuming aging process has hampered efficient production of transparent bar soaps, raising the price to a relatively expensive range.

In the meantime, many attempts have been made to produce transparent bar soaps with a shorter aging period. By way of example, Japanese Patent Laid-open Publication No. S63-275700 discloses a method for continuously producing a transparent bar soap, without using a lower alcohol which has to evaporate in the aging process. From another point of view, Japanese Patent Laid-open Publication No. H11-106307 discloses an improved method for enhancing storage stability of triethanolamine which is added as a neutralizing agent. In this disclosure, a sulfite or the like is blended as a reducing agent. Further, Japanese Patent Laid-open Publication No. H11-124598 discloses a transparent bar soap composition which is efficiently produced by a milling method.

However, as for the production method of Japanese Patent Laid-open Publication No. S63-275700, while the bar soap is stored for a long period, triethanolamine used as the neutralizing agent deteriorates due to oxidation, only to damage the commercial value of the bar soap. Regarding the sweating and clouding phenomenon as mentioned above, this bar soap is likely to sweat during storage, particularly under severe environmental conditions of high temperature and high humidity. In addition, a half-used bar soap suffers from clouding.

In the case of Japanese Patent Laid-open Publication No. H11-106307, it fails to give a satisfactory solution to the above-mentioned problems, despite the incorporation of a sulfite or the like as a reducing agent.

Regrettably, the milled bar soap composition, obtained in Japanese Patent Laid-open Publication No. H11-124598, lacks sufficient transparency.

Bearing these problems in mind, the present invention aims to provide a transparent bar soap composition which can be produced at a high production efficiency, without the aging process indispensable for conventional soap-making methods. The present invention also aims to provide a transparent bar soap composition which is superior in transparency, storage stability and hardness. The present invention further aims to provide a transparent bar soap composition which neither suffers from sweating under the conditions of high temperature and high humidity, nor turns cloudy in the course of use.

SUMMARY OF THE INVENTION

In order to achieve the above objects, the present inventors have made intensive investigations and completed the present invention.

Namely, the present invention relates to a transparent bar soap composition comprising:

- a sodium salt of a fatty acid, or a mixed sodium/potassium salt of a fatty acid;
- at least one amphoteric surfactant selected from the group consisting of compounds represented by following formulas (A) to (C), (A)

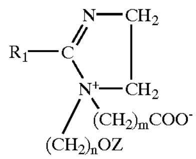

wherein $R_1$ represents an alkyl group having 7 to 21 carbon atoms or an alkenyl group having 7 to 21 carbon atoms, n and m independently represent an interger from 1 to 3, and Z represents a hydrogen atom or $(CH_2)_pCOOY$, wherein p represents an interger from 1 to 3, and Y represents an alkali metal, an alkaline earth metal or an organic amine, (B)

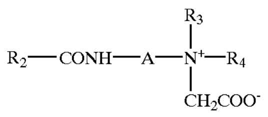

wherein $R_2$ represents an alkyl group having 7 to 21 carbon atoms or an alkenyl group having 7 to 21 carbon atoms, $R_3$ and $R_4$ independently represent a lower alkyl group, and A represents a lower alkylene group, and (C)

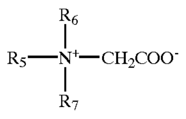

wherein $R_5$ represents an alkyl group having 8 to 22 carbon atoms or an alkenyl group having 8 to 22 carbon atoms, and $R_6$ and $R_7$ independently represent a lower alkyl group;

a nonionic surfactant; and at least one glycerin derivative.

The above-mentioned transparent bar soap composition may comprise 20 to 40% by weight of the sodium salt of a fatty acid or the mixed sodium/potassium salt of a fatty acid, 2 to 10% by weight of the amphoteric surfactant, 2 to 15% by weight of the nonionic surfactant, and 1 to 10% by weight of the glycerin derivative.

In the transparent bar soap composition of the present invention, the molar ratio of sodium to potassium in the mixed sodium/potassium salt of a fatty acid may be from 10/0 to 7/3.

In the transparent bar soap composition of the present invention, the glycerin derivative may be at least one member selected from the group consisting of polyoxypropylene glyceryl ether, polyoxypropylene diglyceryl ether, polyoxypropylene polyglyceryl ether, polyoxyethylene polyoxypropylene glyceryl ether, polyoxyethylene polyoxypropylene diglyceryl ether, and polyoxyethylene polyoxypropylene polyglyceryl ether.

BRIEF DESCRIPTION OF THE DRAWING

The single FIGURE shows a front, vertical section view of a tray used for the hermetic storage test. In this FIGURE, the numeral 1 represents a tray, the numeral 2 represents a bowl, the numeral 3 indicates reserved water, the numeral 4 is a rack, the numerals 5 indicate through-holes, the numerals 6 represent ribs, and the numeral 7 shows a hermetic lid, with A representing a sample.

DISCLOSURE OF THE INVENTION

Figure 1:
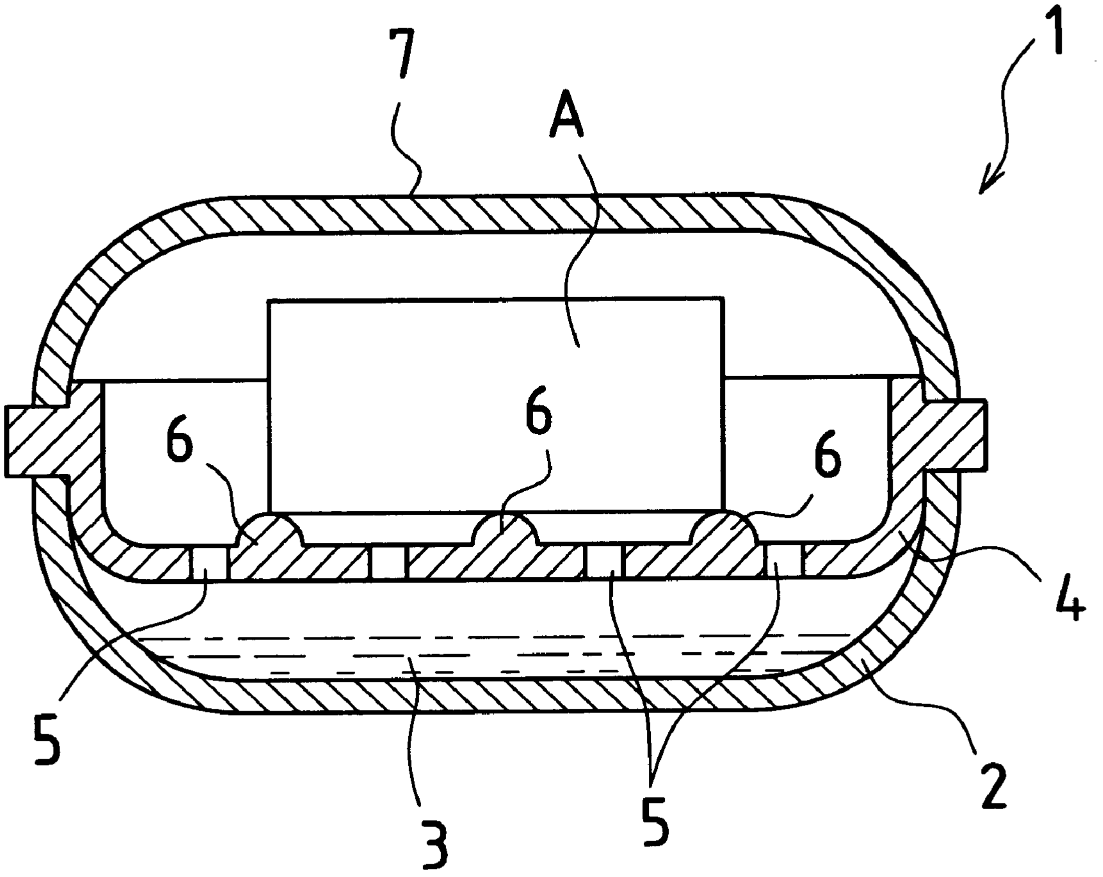

The present invention is hereinafter described in detail. A transparent bar soap composition of the present invention comprises a sodium salt of a fatty acid or a mixed sodium/potassium salt of a fatty acid, together with an amphoteric surfactant, a nonionic surfactant and a glycerin derivative.

In the present transparent bar soap composition, the sodium salt of a fatty acid or the mixed sodium/potassium salt of a fatty acid contains a fatty acid preferably having 8 to 20 carbon atoms, more preferably having 12 to 18 carbon atoms. This fatty acid may be saturated or unsaturated, and may be linear or branched. Typical examples of such fatty acid include lauric acid, myristic acid, palmitic acid, stearic acid, oleic acid, isostearic acid, etc., and also include their mixtures such as beef tallow fatty acid, coconut fatty acid and palm kernel fatty acid.

Examples of the sodium salt of a fatty acid include sodium laurate, sodium myristate, sodium palmitate, sodium stearate, sodium oleate, sodium isostearate, sodium tallowate, sodium cocoate, sodium palm kernelate, etc. They may be used alone or in combination. Among these sodium salts of fatty acids, sodium laurate, sodium myristate, sodium palmitate, sodium stearate, sodium oleate and sodium isostearate are favorable.

Examples of the mixed sodium/potassium salt of a fatty acid include sodium/potassium laurate, sodium/potassium myristate, sodium/potassium palmitate, sodium/potassium stearate, sodium/potassium oleate, sodium/potassium isostearate, sodium/potassium tallowate, sodium/potassium cocoate, sodium/potassium palm kernelate, etc. They may be used alone or in combination. Among these mixed sodium/potassium salts of fatty acids, sodium/potassium laurate, sodium/potassium myristate, sodium/potassium palmitate, sodium/potassium stearate, sodium/potassium oleate and sodium/potassium isostearate are favorable.

In this transparent bar soap composition, the content of the sodium salt of a fatty acid or that of the mixed sodium/potassium salt of a fatty acid is preferably from 20 to 40% by weight, particularly from 25 to 35% by weight. If the content is below 20% by weight, the soap composition has such a low solidifying point that its surface may melt in the course of long-term storage, impairing its commercial value. On the other hand, if the content exceeds 40% by weight, the soap composition may be degraded in transparency or leave a taut feeling after use.

Regarding the mixed sodium/potassium salt of a fatty acid, the molar ratio of sodium to potassium (the sodium/potassium ratio) is preferably from 10/0 (i.e. the sodium salt of a fatty acid) to 7/3, particularly from 9/1 to 8/2. If the content of potassium exceeds the sodium/potassium ratio of 7/3, the soap composition has such a low solidifying point that its surface may melt in the course of long-term storage, impairing its commercial value. In addition, such soap composition may show a decreased hardness, wear away faster in use, sweat under the conditions of high temperature and high humidity, or turn cloudy at the surface in the course of use.

As the amphoteric surfactant for the present transparent bar soap composition, use can be made of the compounds represented by the formulas (A) to (C) in the foregoing section.

In the formula (A), "an alkyl group having 7 to 21 carbon atoms", represented by $R_1$, may be linear or branched, and preferably has 7 to 17 carbon atoms. "An alkenyl group having 7 to 21 carbon atoms", also represented by $R_1$, may be linear or branched, and preferably has 7 to 17 carbon atoms. The symbol Y stands for "an alkali metal" including sodium and potassium, "an alkaline earth metal" including calcium and magnesium, or "an organic amine" including monoethanolamine, diethanolamine and triethanolamine.

Typical examples of the amphoteric surfactants shown by the formula (A) include imidazolinium betaine-type surfactants such as 2-undecyl-N-carboxymethyl-N-hydroxyethylimidazolinium betaine as synthesized from lauric acid (For convenience, it may be also called "lauroylimidazolinium betaine".), 2-heptadecyl-N-carboxymethyl-N-hydroxyethylimidazolinium betaine as synthesized from stearic acid, a mixture of 2-alkyl-N-carboxymethyl-N-hydroxyethylimidazolinium betaine and 2-alkenyl-N-carboxymethyl-N-hydroxyethylimidazolinium betaine (each $R_1$, is a $C_7$–$C_{17}$ alkyl group or a $C_7$–$C_{17}$ alkenyl group) as synthesized from coconut fatty acid (For convenience, it may be also called "cocoylimidazolinium betaine".).

In the formula (B), "an alkyl group having 7 to 21 carbon atoms" and "an alkenyl group having 7 to 21 carbon atoms", both represented by $R_2$, are similar to the ones represented by $R_1$ in the formula (A). "A lower alkyl group", represented by $R_3$ and $R_4$, respectively, may be a linear or branched alkyl group, preferably with 1 to 3 carbon atoms. "A lower alkylene group", represented by A, may be a linear or branched alkylene group, preferably with 3 to 5 carbon atoms.

Typical examples of the amphoteric surfactants shown by the formula (B) (amidoalkyl betaine-type surfactants) are amidopropyl betaine-type surfactants including cocamidopropyl-dimethylaminoacetic acid betaine (a mixture of the compounds in which each $R_2$ is a $C_7$–$C_{17}$ alkyl group or a $C_7$–$C_{17}$ alkenyl group) as synthesized from coconut fatty acid.

In the formula (C), "an alkyl group having 8 to 22 carbon atoms", represented by $R_5$, may be linear or branched, and preferably has 8 to 18 carbon atoms. "An alkenyl group having 8 to 22 carbon atoms", also represented by $R_5$, may be linear or branched, and preferably has 8 to 18 carbon atoms. "A lower alkyl group", represented by $R_6$ and $R_7$, respectively, is similar to the one represented by $R_3$ and $R_4$ in the formula (B).

Typical examples of the amphoteric surfactants shown by the formula (C) (alkyl betaine-type surfactants) are lauryldimethylaminoacetic acid betaine, and a mixture of an alkyldimethylaminoacetic acid betaine and an alkenyldimethylaminoacetic acid betaine (each $R_5$ is a $C_8$–$C_{18}$ alkyl group or a $C_8$–$C_{18}$ alkenyl group) as synthesized from coconut fatty acid.

In the present invention, at least one amphoteric surfactant is selected from the compounds represented by the formulas (A) to (C). Where more than one amphoteric surfactant are employed, such surfactants may be selected only from the compounds of the formula (A), or only from those of the formula (B) or only from those of the formula (C).

Among the above-mentioned amphoteric surfactants, it is particularly suitable to use imidazolinium betaine-type surfactants represented by the formula (A) (above all, cocoylimidazolinium betaine).

The above-mentioned amphoteric surfactant and the fatty acid soap (i.e. the sodium salt of a fatty acid, or the mixed sodium/potassium salt of a fatty acid) form a complex salt. As a result, the transparent bar soap composition of the present invention is improved in transparency and hardness. At the same time, increased hardness results in reduction of the wear rate.

In the present transparent bar soap composition, the content of the amphoteric surfactant is preferably from 2 to 10% by weight, particularly from 4 to 8% by weight. With the content of the amphoteric surfactant being lower than 2% by weight, the soap composition has such a low solidifying point that its surface may melt in the course of long-term storage, impairing its commercial value. Besides, the soap composition may have a decreased hardness and wear away faster through use. Furthermore, the soap composition may be degraded in transparency. Conversely, when the content of the amphoteric surfactant exceeds 10% by weight, the soap composition may leave a sticky feeling after use. Also, the soap composition may turn brown at the surface through long-term storage, damaging its commercial value.

As the nonionic surfactant for the transparent bar soap composition of the present invention, there may be mentioned polyoxyethylene (also called POE) hydrogenated caster oil, polyoxyethylene 2-octyldodecyl ether, polyoxyethylene lauryl ether, propylene oxide-ethylene oxide block copolymer, polyoxyethylene polyoxypropylene cetyl ether, polyoxyethylene polyoxypropylene glycol, polyethylene glycol diisostearate, alkyl glucosides, polyoxyethylene-modified silicones (e.g. polyoxyethylene alkyl-modified dimethylsilicones), polyoxyethylene glycerin monostearate, polyoxyethylene alkyl glucosides, etc. These nonionic surfactants may be used alone or in combination. Among them, polyoxyethylene hydrogenated caster oil and propylene oxide-ethylene oxide block copolymer can be used with advantage.

Addition of the nonionic surfactant can enhance transparency of the transparent bar soap composition of the present invention.

In the present transparent bar soap composition, the content of the nonionic surfactant is preferably from 2 to 15% by weight, particularly from 6 to 12% by weight. When the content is lower than 2% by weight, the resulting soap composition may be degraded in transparency or leave a taut feeling after use. In contrast, when the content exceeds 15% by weight, the soap composition has such a low solidifying point that its surface may melt in the course of long-term storage, impairing its commercial value. Besides, the soap composition may have a decreased hardness and wear away faster through use. It may also leave a sticky feeling after use.

Regarding the glycerin derivative for the transparent bar soap composition of the present invention, suitable glycerin derivatives include polyoxypropylene glyceryl ether, polyoxypropylene diglyceryl ether, polyoxypropylene polyglyceryl ether, polyoxyethylene polyoxypropylene glyceryl ether, polyoxyethylene polyoxypropylene diglyceryl ether, polyoxyethylene polyoxypropylene polyglyceryl ether, etc. These glycerin derivatives may be used alone or in combination. Among them, it is particularly desirable to employ polyoxypropylene(9) diglyceryl ether, polyoxypropylene(7) glyceryl ether.

In the transparent bar soap composition of the present invention, the content of the glycerin derivative is preferably from 1 to 10% by weight, particularly from 4 to 8% by weight. If its content is less than 1% by weight, the soap composition has such a low solidifying point that its surface may melt in the course of long-term storage, impairing its commercial value. Besides, the soap composition may sweat under the conditions of high temperature and high humidity. On the other hand, if its content is over 10%, the resulting soap composition may show degraded transparency or excessive hardness, and leave a sticky feeling after use.

Incorporation of the glycerin derivative contributes to the production of the present transparent bar soap composition not only by raising the solidifying point of the neat soap but also by reducing its hygroscopic property.

Additionally, unless the above-mentioned effects are adversely affected, the transparent bar soap composition may contain optional ingredients. The optional ingredients include bactericides such as trichlorocarbanilide and hinokitiol; humectants such as maltitol, sorbitol, glycerin, 1,3-butylene glycol, propylene glycol, sugar, pyrrolidone carboxylic acid, sodium pyrrolidone carboxylate, hyaluronic acid and polyoxyethylene alkyl glucoside ether; oils; fragrances; colorants; chelating agents such as trisodium edetate (EDTA-3Na) dihydrate; UV-absorbing agents; antioxidants; natural extracts such as dipotassium glycyrrhizinate, plantain extract, lecithin, saponin, aloe, phellodendron bark and wild chamomile; nonionic, cationic or anionic water-soluble polymers; skin-feel improvers such as lactic acid esters; foaming improvers such as sodium alkyl ether carboxylates, disodium alkyl sulfosuccinates, sodium alkylisethionates, sodium polyoxyethylene alkyl sulfates, acylmethyltaurines, sodium acylglutamates and sodium acylsarcosinates; and others.

To manufacture the transparent bar soap composition of the present invention, general processes such as the framing method and the milling method are applicable to mixtures of the above-mentioned ingredients.

EXAMPLES

Hereinafter, the present invention is described in more detail by means of Examples and Comparative Examples. It should be understood, however, these examples do not limit the scope of the present invention.

Examples 1 to 5

First of all, a mixed fatty acid was prepared according to the formulation given in Table 1, and neutralized with an aqueous solution of sodium hydroxide. The neutralized mixture was dried to give the sodium salt of the mixed fatty acid.

TABLE 1

| MIXED FATTY ACID | |
|---|---|
| Mixed ingredients | Mixed amounts (parts by weight) |
| Lauric acid | 20 |
| Myristic acid | 40 |
| Palmitic acid | 15 |
| Stearic acid | 20 |
| Oleic acid | 5 |

Secondly, based on the formulation given in Table 2, transparent bar soap compositions of Examples 1 to 5 were produced by the process described below. Among these soap compositions, the amount of the sodium salt of the mixed fatty acid was different from each other.

TABLE 2

| | Examples | | | | |
|---|---|---|---|---|---|
| Compounded ingredients | 1 | 2 | 3 | 4 | 5 |
| Sodium salt of mixed fatty acid | 20 | 25 | 30 | 35 | 40 |
| Cocoylimidazolinium betaine | 5 | 5 | 5 | 5 | 5 |
| Polyoxyethylene (60) hydrogenated caster oil | 10 | 10 | 10 | 10 | 10 |
| Polyoxypropylene (14) diglyceryl ether | 5 | 5 | 5 | 5 | 5 |
| Sugar | 14 | 9 | 4 | 4 | 4 |
| Sorbitol | 10 | 10 | 10 | 5 | — |
| Glycerin | 15 | 15 | 15 | 15 | 15 |
| EDTA-3Na dihydrate | 0.1 | 0.1 | 0.1 | 0.1 | 0.1 |
| Fragrance | 1 | 1 | 1 | 1 | 1 |
| Ion exchange water | *R | R | R | R | R |

Unit: % by weight
*R means "the rest".

Specifically, the sodium salt of the mixed fatty acid, glycerin, sorbitol and polyoxypropylene(14) diglyceryl ether were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(60) hydrogenated caster oil, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

Samples of the transparent bar soap compositions obtained in Examples 1 to 5 were tested for the items listed in Table 3.

TABLE 3

| | Examples | | | | |
|---|---|---|---|---|---|
| Test items | 1 | 2 | 3 | 4 | 5 |
| Solidifying point (° C.) | 55 | 57 | 60 | 62 | 63 |
| Transparency | excellent | excellent | excellent | excellent | good |
| Hardness | 21 | 24 | 26 | 30 | 35 |
| Sweating test | good | excellent | excellent | excellent | excellent |
| Hermetic storage test | good | excellent | excellent | excellent | excellent |
| Wear rate | good | excellent | excellent | excellent | excellent |
| Elution rate | good | excellent | excellent | excellent | excellent |
| Foaming property | good | excellent | excellent | excellent | excellent |
| Feeling after washing | good | excellent | excellent | excellent | good |
| Condition stability at 45° C. | good | excellent | excellent | excellent | excellent |
| Appearance stability at 45° C. | good | good | good | good | good |

The tests listed in Table 3 were carried out in the following manners.

1. Solidifying Point

To measure the solidifying point, the neat soap was poured into a resin cup and stirred slowly by means of a mercury thermometer. The stirring was continued while the temperature was dropping. When the neat soap solidified so hard as to render the stirring difficult, the temperature was measured as the solidifying point.

2. Transparency

Transparency was judged by visual observation and graded by the following criteria.

| | |
|---|---|
| Excellent: | Highly uniformly transparent |
| Good: | Uniformly transparent |
| Fair: | Slightly opaque (negligible) |
| Bad: | Opaque |

3. Hardness

Hardness was measured with the use of Card tension meter manufactured by Itao electric incorporated company. At a temperature of 25° C., 800 grams of load was imposed on each sample by a needle having a diameter of 1 mm.

4. Sweating Test

For the sweating test, each sample was left in an environment control device regulated at 40° C., 75% RH. A week later, the sample was removed from the environment control device and dried at 25° C. for 12 hours. After drying, the surface of each sample was visually evaluated by the following criteria.

| | |
|---|---|
| Excellent: | No sweating |
| Good: | Very slight (negligible) sweating |
| Fair: | Slight sweating |
| Bad: | Heavy sweating with a mushy surface |

5. Hermetic Storage Test (Clouding Degree at the Surface of Half-used Soap Compositions)

For the hermetic storage test, the surface of each sample was lightly wetted with warm water (28 to 32° C.) and rubbed with both hands to make foam. The foam covering the surface of the sample was lightly washed away with water, and then the water remaining on the sample was shaken off for a few times. Finally, the sample was put in a tray 1 illustrated in FIG. 1. This procedure was repeated twice a day (in the morning and the evening), five days a week, for a total of 40 days.

Referring to FIG. 1, the tray 1 has a bowl 2 and a hermetic lid 7, with a shallow pool of water 3 being reserved at the bottom of the bowl 2. The periphery of the bowl 2 holds a rack 4, the bottom of which includes through-holes 5 and ribs 6. The sample A is rested on the rack 4 and hermetically kept in the tray 1 which is closed by a hermetic lid 7. While the sample A is housed in the tray 1, the through-holes 5 and the ribs 6 allow water to drain off from the sample A. At the same time, the through-holes 5 pass vapors generating from the reserved water 3 to humidify the sample A.

The tray 1 containing the sample A was stored for a total of 40 days in a room where the environmental conditions were constantly controlled at 30° C. and 70% RH, using a ventilating fan or the like. When the room temperature was not higher than 10° C., or when the humidity was not higher than 50% RH, the environmental conditions in the room were adjusted by feeding water (high or ambient temperature) into a bath equipped inside the room. After 40 days of storage, the surface of the sample A was visually observed for cloudiness and mushiness. The result of the hermetic storage test was graded by the following criteria.

| | |
|---|---|
| Excellent: | Neither mushy nor cloudy |
| Good: | Slightly mushy (negligible) |
| Fair: | Slightly cloudy (negligible) |
| Bad: | Both mushy and cloudy |

6. Wear Rate

The wear rate was measured according to JIS K 3304 and graded by the following criteria.

| | |
|---|---|
| Excellent: | Less than 30 |
| Good: | 30 (inclusive) to 40 (exclusive) |
| Fair: | 40 (inclusive) to 50 (exclusive) |
| Bad: | 50 or higher |

7. Elution Rate

To obtain the elution rate, each sample had its weight measured, and attached at the tip of a wire. In the next step, this sample was immersed in water (20° C.) for an hour. Thereafter, the sample was pulled out of the water and had its weight measured again. The elution rate was calculated, using the measured values and the expression given below. The evaluation was based on the following criteria.

| | |
|---|---|
| Excellent: | Less than 10% |
| Good: | 10% (inclusive) to 20% (exclusive) |
| Fair: | 20% (inclusive) to 30% (exclusive) |
| Bad: | 30% or higher |

Elution rate (%)=$100\times(W_1-W_2)/W_1$ ($W_1$: Weight (g) of the sample before immersion, $W_2$: Weight (g) of the sample after immersion)

8. Foaming Property

To evaluate the foaming property, the surface of each sample was lightly wetted with warm water (28 to 32° C.) and rubbed 20 to 30 times within both hands to make foam. The condition of foaming was judged by the following criteria.

| | |
|---|---|
| Excellent: | Remarkable foaming |
| Good: | Good foaming |
| Fair: | Fair foaming |
| Bad: | Poor foaming |

9. Feeling After Washing

For judgement of feeling after washing, twenty female subjects (in the twenties and thirties) were requested to foam each sample in their hands and to wash their face, just as they normally did. After washing, the condition of the skin was judged by the following criteria.

| | |
|---|---|
| Excellent: | Remarkably moist |
| Good: | Well moist |
| Fair: | Fairly moist |
| Bad: | Sticky or taut |

10. Condition Stability at 45° C.

To test the condition stability at 45° C., each sample was air-tightly wrapped with a resin film and left for one month at a 45° C. environment. Later, the surface condition of the sample was visually observed and graded by the following criteria.

| | |
|---|---|
| Excellent: | No change |
| Good: | Very slightly melted (negligible) |
| Fair: | Slightly melted |
| Bad: | Melted and softened |

11. Appearance Stability at 45° C.

To test the appearance stability at 45° C., each sample was air-tightly wrapped with a resin film and left for one month at a 45° C. environment. Later, the surface condition of the sample was visually observed and graded by the following criteria.

| | |
|---|---|
| Excellent: | No change |
| Good: | Very slightly brown (negligible) |
| Fair: | Slightly brown |
| Bad: | Noticeably brown |

With regard to the transparent bar soap compositions manufactured without the aging process, the results compiled in Table 3 proved that the samples of Examples 1 to 5 had advantageous properties in transparency and hardness.

Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

Examples 6 to 8

To begin with, a mixed fatty acid was prepared according to the formulation given in Table 4, and neutralized with an aqueous solution of sodium hydroxide. The neutralized mixture was dried to give the sodium salt of the mixed fatty acid.

TABLE 4

MIXED FATTY ACID

| Mixed ingredients | Mixed amounts (parts by weight) |
|---|---|
| Lauric acid | 20 |
| Myristic acid | 10 |
| Palmitic acid | 20 |
| Stearic acid | 30 |
| Oleic acid | 35 |

Secondly, based on the formulation given in Table 5, transparent bar soap compositions of Examples 6 to 8 were produced by the process described below. Among these soap compositions, the amount of cocoylimidazolinium betaine was different from each other.

TABLE 5

| | Examples | | |
|---|---|---|---|
| Compounded ingredients | 6 | 7 | 8 |
| Sodium salt of mixed fatty acid | 25 | 25 | 25 |
| Cocoylimidazolinium betaine | 2 | 7 | 10 |
| Polyoxyethylene (60) hydrogenated caster oil | 10 | 10 | 10 |
| Polyoxypropylene (8) glyceryl ether | 5 | 5 | 5 |
| Sugar | 14 | 14 | 14 |
| Sorbitol | 15 | 10 | 7 |
| Glycerin | 4 | 4 | 4 |
| EDTA-3Na dihydrate | 0.1 | 0.1 | 0.1 |
| Fragrance | 1 | 1 | 1 |
| Ion exchange water | *R | R | R |

Unit: % by weight
*R means "the rest".

Specifically, the sodium salt of the mixed fatty acid, glycerin, sorbitol and polyoxypropylene (8) glyceryl ether were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(60) hydrogenated caster oil, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

Samples of the transparent bar soap compositions obtained in Examples 6 to 8 were tested for the items listed in Table 6.

TABLE 6

| | Examples | | |
|---|---|---|---|
| Test items | 6 | 7 | 8 |
| Solidifying point (° C.) | 55 | 61 | 63 |
| Transparency | good | excellent | good |
| Hardness | 22 | 28 | 30 |
| Sweating test | good | excellent | excellent |
| Hermetic storage test | good | excellent | excellent |
| Wear rate | good | excellent | excellent |
| Elution rate | good | excellent | excellent |
| Foaming property | good | excellent | excellent |
| Feeling after washing | good | excellent | good |
| Condition stability at 45° C. | good | excellent | excellent |
| Appearance stability at 45° C. | excellent | excellent | good |

In these Examples, the solidifying point and other test items were tested and evaluated in the same manner as mentioned in Example 1.

With regard to the transparent bar soap compositions manufactured without the aging process, the results compiled in Table 6 proved that the samples of Examples 6 to 8 had advantageous properties in transparency and hardness. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

Examples 9 to 12

To begin with, a mixed fatty acid was prepared according to the formulation given in Table 7, and neutralized with an aqueous solution of sodium hydroxide. The neutralized mixture was dried to give the sodium salt of the mixed fatty acid.

TABLE 7

MIXED FATTY ACID

| Mixed ingredients | Mixed amounts (parts by weight) |
|---|---|
| Myristic acid | 30 |
| Palmitic acid | 15 |
| Stearic acid | 20 |
| Oleic acid | 35 |

Secondly, based on the formulation given in Table 8, transparent bar soap compositions of Examples 9 to 12 were produced by the process described below. Among these soap compositions, the amount of polyoxyethylene(35) polyoxypropylene(40) glycol was different from each other.

TABLE 8

| | Examples | | | |
|---|---|---|---|---|
| Compounded ingredients | 9 | 10 | 11 | 12 |
| Sodium salt of mixed fatty acid | 30 | 30 | 30 | 30 |
| Cocoylimidazolinium betaine | 5 | 5 | 5 | 5 |
| Polyoxyethylene (35) polyoxypropylene (40) glycol | 2 | 8 | 12 | 15 |
| Polyoxyethylene (10) polyoxypropylene (10) | 5 | 5 | 5 | 5 |

TABLE 8-continued

| Compounded ingredients | Examples 9 | 10 | 11 | 12 |
|---|---|---|---|---|
| glyceryl ether | | | | |
| Sugar | 12 | 6 | 4 | 4 |
| Sorbitol | 10 | 10 | 8 | 5 |
| Glycerin | 15 | 15 | 15 | 15 |
| EDTA-3Na dihydrate | 0.1 | 0.1 | 0.1 | 0.1 |
| Fragrance | 1 | 1 | 1 | 1 |
| Ion exchange water | *R | R | R | R |

Unit: % by weight
*R means "the rest".

Specifically, the sodium salt of the mixed fatty acid, glycerin, sorbitol and polyoxyethylene(10) polyoxypropylene(10) glyceryl ether were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(35) polyoxypropylene (40) glycol, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

Samples of the transparent bar soap compositions obtained in Examples 9 to 12 were tested for the items listed in Table 9.

TABLE 9

| Test items | Examples 9 | 10 | 11 | 12 |
|---|---|---|---|---|
| Solidifying point (° C.) | 60 | 58 | 56 | 54 |
| Transparency | good | excellent | excellent | excellent |
| Hardness | 30 | 27 | 24 | 22 |
| Sweating test | good | excellent | excellent | good |
| Hermetic storage test | good | excellent | excellent | good |
| Wear rate | good | excellent | excellent | good |
| Elution rate | good | excellent | excellent | good |
| Foaming property | good | good | good | good |
| Feeling after washing | good | excellent | excellent | good |
| Condition stability at 45° C. | good | good | good | good |
| Appearance stability at 45° C. | good | good | good | good |

In these Examples, the solidifying point and other test items were tested and evaluated in the same manner as mentioned in Example 1.

With regard to the transparent bar soap compositions manufactured without the aging process, the results compiled in Table 9 proved that the samples of Examples 9 to 12 had advantageous properties in transparency and hardness. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

Examples 13 to 15 and Comparative Examples 1 to 3

To begin with, a mixed fatty acid was prepared according to the formulation given in Table 10, and neutralized with an aqueous solution of sodium hydroxide. The neutralized mixture was dried to give the sodium salt of the mixed fatty acid.

TABLE 10

MIXED FATTY ACID

| Mixed ingredients | Mixed amounts (parts by weight) |
|---|---|
| Lauric acid | 20 |
| Myristic acid | 40 |
| Palmitic acid | 15 |
| Stearic acid | 20 |
| Isostearic acid | 5 |

Secondly, based on the formulation given in Table 11, transparent bar soap compositions of Examples 13 to 15 were produced by the process described below. Among these soap compositions, the amount of polyoxypropylene (10) glyceryl ether was different from each other.

TABLE 11

| Compounded ingredients | Examples 13 | 14 | 15 | Comparative Examples 1 | 2 | 3 |
|---|---|---|---|---|---|---|
| Sodium salt of mixed fatty acid | 30 | 30 | 30 | 30 | 30 | 30 |
| Cocoylimidazolinium betaine | 5 | 5 | 5 | 5 | 5 | 5 |
| Polyoxyethylene (20) polyoxypropylene (8) cetyl ether | 10 | 10 | 10 | 10 | 10 | 10 |
| Polyoxypropylene (10) glyceryl ether | 1 | 6 | 10 | — | — | — |
| Sugar | 4 | 4 | 4 | 4 | 4 | 4 |
| Sorbitol | 10 | 10 | 10 | 10 | 10 | 10 |
| Glycerin | 15 | 15 | 11 | 15 | 15 | 21 |
| 1,3-Butylene glycol | 5 | — | — | 6 | — | — |
| Propylene glycol | — | — | — | — | 6 | — |
| EDTA-3Na dihydrate | 0.1 | 0.1 | 0.1 | 0.1 | 0.1 | 0.1 |
| Fragrance | 1 | 1 | 1 | 1 | 1 | 1 |
| Ion exchange water | *R | R | R | R | R | R |

Unit: % by weight
*R means "the rest".

Specifically, the sodium salt of the mixed fatty acid, glycerin, sorbitol and polyoxypropylene(10) glyceryl ether were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(20) polyoxypropylene(8) cetyl ether, the remaining ion exchange water, 1,3-butylene glycol, propylene glycol and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

As for Comparative Examples 1 to 3, the transparent bar soap compositions were manufactured in the above-mentioned manner, but without blending polyoxypropylene (10) glyceryl ether as the glycerin derivative.

Samples of the transparent bar soap compositions obtained in Examples 13 to 15 and Comparative Examples 1 to 3 were tested for the items listed in Table 12.

TABLE 12

| | Examples | | | Comparative Examples | | |
|---|---|---|---|---|---|---|
| Test items | 13 | 14 | 15 | 1 | 2 | 3 |
| Solidifying point (° C.) | 55 | 59 | 62 | 52 | 51 | 50 |
| Transparency | good | excellent | good | fair | good | good |
| Hardness | 23 | 27 | 29 | 19 | 17 | 15 |
| Sweating test | good | excellent | good | bad | bad | bad |
| Hermetic storage test | good | excellent | excellent | bad | bad | bad |
| Wear rate | good | excellent | excellent | fair | fair | fair |
| Elution rate | good | excellent | excellent | fair | fair | fair |
| Foaming property | good | good | good | good | good | good |
| Feeling after washing | good | excellent | good | good | good | good |
| Condition stability at 45° C. | good | good | good | bad | bad | bad |
| Appearance stability at 45° C. | good | good | good | good | good | good |

In these Examples and Comparative Examples, the solidifying point and other test items were tested and evaluated in the same manner as mentioned in Example 1.

With regard to the transparent bar soap compositions manufactured without the aging process, the results compiled in Table 12 proved that the samples of Examples 13 to 15 had advantageous properties in transparency and hardness. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

On the contrary, the results of the samples of Comparative Examples 1 to 3 showed disadvantages of omitting polyoxypropylene(10) glyceryl ether. Firstly, due to the solidifying point not higher than 52° C., the surface of the samples melted easily, impairing its commercial value. Secondly, because of the decrease in hardness, which raised both the wear rate and the elution rate, the samples wore away faster through use. Thirdly, the comparative samples tended to sweat under the hot and humid conditions. And lastly, in the course of use, they turned cloudy at the surface.

Examples 16 to 19

To begin with, a mixed fatty acid was prepared according to the formulation given in Table 1. This mixed fatty acid was neutralized with an aqueous solution of sodium hydroxide, or with an aqueous solution blend of sodium hydroxide/potassium hydroxide (sodium/potassium molar ratio: 9/1–7/3). Each neutralized mixture was dried to give the salt of the mixed fatty acid.

Secondly, based on the formulation given in Table 13, transparent bar soap compositions of Examples 16 to 19 were produced by the process described below. Among these soap compositions, the sodium/potassium molar ratio in the salt of the mixed fatty acid was different from each other.

TABLE 13

| | Examples | | | |
|---|---|---|---|---|
| Compounded ingredients | 16 | 17 | 18 | 19 |
| Salt of mixed fatty acid (molar ratio of sodium/potassium) | 30 (10/0) | 30 (9/1) | 30 (8/2) | 30 (7/3) |
| Cocoylimidazolinium betaine | 5 | 5 | 5 | 5 |
| Polyoxyethylene (12) lauryl ether | 10 | 10 | 10 | 10 |
| Polyoxyethylene (20) polyoxypropylene (20) tetraglyceryl ether | 5 | 5 | 5 | 5 |
| Sugar | 4 | 4 | 4 | 4 |
| Sorbitol | 10 | 10 | 10 | 10 |
| Glycerin | 15 | 15 | 15 | 15 |
| EDTA-3Na dihydrate | 0.1 | 0.1 | 0.1 | 0.1 |
| Fragrance | 1 | 1 | 1 | 1 |
| Ion exchange water | *R | R | R | R |

Unit: % by weight
*R means "the rest".

Specifically, the salt of the mixed fatty acid, glycerin, sorbitol and polyoxyethylene(20) polyoxypropylene(20) tetraglyceryl ether were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(12) lauryl ether, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

Samples of the transparent bar soap compositions obtained in Examples 16 to 19 were tested for the items listed in Table 14.

TABLE 14

| | Examples | | | |
|---|---|---|---|---|
| Test items | 16 | 17 | 18 | 19 |
| Solidifying point (° C.) | 59 | 57 | 56 | 54 |
| Transparency | good | excellent | excellent | good |
| Hardness | 29 | 28 | 26 | 23 |
| Sweating test | excellent | excellent | excellent | good |
| Hermetic storage test | excellent | excellent | excellent | good |
| Wear rate | excellent | excellent | excellent | good |
| Elution rate | good | excellent | excellent | good |
| Foaming property | good | good | good | good |
| Feeling after washing | good | good | good | good |
| Condition stability at 45° C. | good | good | good | good |
| Appearance stability at 45° C. | good | good | good | good |

In these Examples, the solidifying point and other test items were tested and evaluated in the same manner as mentioned in Example 1.

With regard to the transparent bar soap compositions manufactured without the aging process, the results compiled in Table 14 proved that the samples of Examples 16 to 19 had advantageous properties in transparency and hardness. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

Examples 20 to 22

To begin with, a mixed fatty acid was prepared according to the formulation given in Table 1, and neutralized with an aqueous solution blend of sodium hydroxide/potassium hydroxide (sodium/potassium molar ratio: 9/1). The neutralized mixture was dried to give the salt of the mixed fatty acid.

Secondly, based on the formulation given in Table 15, transparent bar soap compositions of Examples 20 to 22 were produced by the process described below. Among these soap compositions, the type of amphoteric surfactants was different from each other.

TABLE 15

| | Examples | | |
|---|---|---|---|
| Compounded ingredients | 20 | 21 | 22 |
| Salt of mixed fatty acid | 30 | 30 | 30 |
| Cocoylimidazolinium betaine | 5 | — | — |
| Cocamidopropyldimethylamino-acetic acid betaine | — | 5 | — |
| Lauryldimethylaminoacetic acid betaine | — | — | 5 |
| Polyoxyethylene (5) glycerin monostearate | 10 | 10 | 10 |
| Polyoxypropylene (70) glyceryl ether | 5 | 5 | 5 |
| Sugar | 4 | 4 | 4 |
| Sorbitol | 10 | 10 | 10 |
| Glycerin | 15 | 15 | 15 |
| EDTA-3Na dihydrate | 0.1 | 0.1 | 0.1 |
| Fragrance | 1 | 1 | 1 |
| Ion exchange water | *R | R | R |

Unit: % by weight
*R means "the rest".

Specifically, the salt of the mixed fatty acid, glycerin, sorbitol and polyoxypropylene(70) glyceryl ether were dissolved at a temperature of 75 to 85° C. Fed into this mixture was a solution in which EDTA-3Na dihydrate was dissolved in some of the ion exchange water. Further, sugar, the amphoteric surfactant, polyoxyethylene(5) glycerin monostearate, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

Samples of the transparent bar soap compositions obtained in Examples 20 to 22 were tested for the items listed in Table 16.

TABLE 16

| | Examples | | |
|---|---|---|---|
| Test items | 20 | 21 | 22 |
| Solidifying point (° C.) | 59 | 56 | 55 |
| Transparency | excellent | good | good |
| Hardness | 29 | 27 | 25 |
| Sweating test | excellent | good | good |
| Hermetic storage test | excellent | good | good |
| Wear rate | excellent | good | good |
| Elution rate | excellent | good | good |
| Foaming property | excellent | good | good |
| Feeling after washing | good | good | good |
| Condition stability at 45° C. | good | good | good |
| Appearance stability at 45° C. | good | good | good |

In these Examples, the solidifying point and other test items were tested and evaluated in the same manner as mentioned in Example 1.

With regard to the transparent bar soap compositions manufactured without the aging process, the results compiled in Table 16 proved that the samples of Examples 20 to 22 had advantageous properties in transparency and hardness. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

In addition, comparison between Example 20 and Examples 21/22 indicates that imidazolinium betaine-type surfactants are particularly preferable among various types of amphoteric surfactants. According to the above results, the imidazolinium betaine-type surfactant was superior in terms of transparency, hardness, sweating under the hot and humid conditions, clouding at the surface of a half-used product, foaming property, etc.

Examples 23 to 27 and Comparative Examples 4 and 5

To begin with, a mixed fatty acid was prepared according to the formulation given in Table 1, and neutralized with an aqueous solution blend of sodium hydroxide/potassium hydroxide (sodium/potassium molar ratio: 9/1). The neutralized mixture was dried to give the salt of the mixed fatty acid.

Secondly, based on the formulation given in Table 17, transparent bar soap compositions of Examples 23 to 27 were produced by the process described below. Among these soap compositions, the kind of glycerin derivatives was different from each other.

TABLE 17

| Compounded | | Examples | | | | | Comp. Examples | |
|---|---|---|---|---|---|---|---|---|
| ingredients | | 23 | 24 | 25 | 26 | 27 | 4 | 5 |
| Salt of mixed fatty acid | | 30 | 30 | 30 | 30 | 30 | 30 | 30 |
| Cocoylimidazolinium betaine | | 5 | 5 | 5 | 5 | 5 | 5 | 5 |
| Polyoxyethylene (10) methyl glucoside | | 10 | 10 | 10 | 10 | 10 | 10 | 10 |
| Glycerin derivative | a | 5 | — | — | — | — | — | — |
| | b | — | 5 | — | — | — | — | — |
| | c | — | — | 5 | — | — | — | — |
| | d | — | — | — | 5 | — | — | — |
| | e | — | — | — | — | 5 | — | — |
| Non-glycerin derivative | f | — | — | — | — | — | 5 | — |
| | g | — | — | — | — | — | — | 5 |
| Sugar | | 4 | 4 | 4 | 4 | 4 | 4 | 4 |
| Sorbitol | | 10 | 10 | 10 | 10 | 10 | 10 | 10 |
| Glycerin | | 15 | 15 | 15 | 15 | 15 | 15 | 15 |
| EDTA-3Na dihydrate | | 0.1 | 0.1 | 0.1 | 0.1 | 0.1 | 0.1 | 0.1 |
| Fragrance | | 1 | 1 | 1 | 1 | 1 | 1 | 1 |
| Ion exchange water | | *R | R | R | R | R | R | R |

Unit: % by weight
*R means "the rest".

Specifically, the salt of the mixed fatty acid, glycerin, sorbitol and the glycerin derivative a–e were dissolved at a temperature of 75 to 85° C. Fed into this mixture was a solution in which EDTA-3Na dihydrate was dissolved in some of the ion exchange water. Further, sugar, cocoylimidazolinium betaine, polyoxyethylene(10) methyl glucoside, the remaining ion exchange water and fragrance were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

For Comparative Examples 4 and 5, transparent bar soap compositions were obtained in the above-mentioned manner, except for replacing the glycerin derivative with non-glycerin derivatives f and g, respectively.

The glycerin derivatives a–e and the non-glycerin derivatives f and g are named in Table 18.

TABLE 18

| | | |
|---|---|---|
| Glycerin derivative | a | Polyoxypropylene (9) diglyceryl ether |
| | b | Polyoxypropylene (7) glyceryl ether |
| | c | Polyoxypropylene (14) diglyceryl ether |
| | d | Polyoxyethylene (24) polyoxypropylene (24) glyceryl ether |
| | e | Polyoxypropylene (24) glyceryl ether |
| Non-glycerin | f | Polyethylene glycol 1500 |
| Derivative | g | Polypropylene glycol |

Samples of the transparent bar soap compositions obtained in Examples 23 to 27 and Comparative Examples 4 and 5 were tested for the items listed in Table 19.

TABLE 19

| | Examples | | | | | Comparative Examples | |
|---|---|---|---|---|---|---|---|
| Test items | 23 | 24 | 25 | 26 | 27 | 4 | 5 |
| Solidifying point (° C.) | 59 | 61 | 57 | 60 | 59 | 52 | 51 |
| Transparency | excellent | excellent | good | good | good | good | good |
| Sweating test | excellent | excellent | good | good | good | fair | fair |
| Hermetic storage test | excellent | excellent | good | good | good | bad | bad |
| Wear rate | excellent | excellent | good | good | good | bad | bad |
| Elution rate | excellent | excellent | good | good | good | bad | bad |
| Foaming property | excellent | excellent | good | good | good | good | good |
| Feeling after washing | excellent | excellent | good | good | good | good | good |
| Condition stability at 45° C. | good | good | good | good | good | bad | bad |
| Appearance stability at 45° C. | good | good | good | good | good | good | good |

In these Examples and Comparative Examples, the solidifying point and other test items were tested and evaluated in the same manner as mentioned in Example 1.

With regard to the transparent bar soap compositions manufactured without the aging process, the results compiled in Table 19 proved that the samples of Examples 23 to 27 showed an advantageous property in transparency. Besides, these samples did not deteriorate in their surface condition and appearance (i.e. no melting and discoloration), even after the long-term storage in the severe environmental condition at 45° C. Further, they did not sweat under the hot and humid conditions. The surface of the samples did not turn cloudy in the course of use.

On the contrary, the results of the samples of Comparative Examples 4 and 5 showed disadvantages of blending a non-glycerin derivative instead of a glycerin derivative. Firstly, due to the solidifying point not higher than 52° C., the surface of the samples melted easily, impairing its commercial value. Secondly, increase in the wear rate and the elution rate caused the samples to wear away faster through use. Thirdly, the comparative samples tended to sweat under the hot and humid conditions. And lastly, in the course of use, they turned cloudy at the surface.

In contrast, the samples which contained a glycerin derivative had remarkable properties as the transparent bar soap composition, irrespective of the kind of glycerin derivatives. In particular, comparison between Examples 23/24 and Examples 25–27 confirms that preferable glycerin derivatives are polyoxypropylene(9) diglyceryl ether and polyoxy-propylene(7) glyceryl ether.

Example 28

Based on the formulation given in Table 20, the transparent bar soap composition of Example 28 was produced by the process described below.

TABLE 20

| Compounded ingredients | Example 28 (weight %) |
|---|---|
| Lauric acid | 4.5 |
| Myristic acid | 9 |
| Palmitic acid | 3 |
| Stearic acid | 5 |
| Isostearic acid | 3 |
| 48% Aqueous sodium hydroxide | 6.7 |
| 48% Aqueous potassium hydroxide | 2.3 |
| Glycerin | 12 |
| 70% Sorbitol | 5 |
| Polyoxypropylene (7) glyceryl ether | 5 |
| EDTA-3Na dihydrate | 0.1 |

TABLE 20-continued

| Compounded ingredients | Example 28 (weight %) |
|---|---|
| Sugar | 12 |
| Lauroylimidazolinium betaine | 4 |
| Polyoxyethylene (5) glycerin monostearate | 10 |
| Fragrance | 0.5 |
| Red No. 227 (Fast acid magenta) | 0.0005 |
| Dipotassium glycyrrhizinate | 0.1 |
| Ion exchange water | the rest |

Specifically, at a temperature of 65 to 75° C., lauric acid, myristic acid, palmitic acid, stearic acid and isostearic acid were dissolved together with glycerin, 70% sorbitol and polyoxypropylene(7) glyceryl ether. This solution was neutralized by addition of 48% aqueous sodium hyroxide and 48% aqueous potassium hydroxide. Fed into this mixture was a solution in which EDTA-3Na dihydrate was dissolved in some of the ion exchange water. Then, at a temperature of 75 to 85° C., sugar, lauroylimidazolinium betaine, polyoxyethylene(5) glycerin monostearate, the remaining ion exchange water, fragrance, Red No. 227 (fast acid magenta) and dipotassium glycyrrhizinate were added to make a neat soap. The neat soap was poured into a frame made of a 70-mm-diameter pipe. With keeping the frame at 30° C. with warm water, the neat soap was cooled for two hours for solidification. Thereafter, the solid product was cut into a 100-gram transparent bar soap composition.

The transparent bar soap composition of Example 28, obtained without the aging process, had advantageous properties in transparency and hardness. Besides, his soap composition did not deteriorate in its surface condition and appearance (i.e. no melting and discoloration), even after the long-term storage in the severe environmental condition at 45° C. Further, the soap composition did not sweat under the hot and humid conditions, nor did its surface turn cloudy in the course of use.

Example 29

Based on the formulation given in Table 21, the transparent bar soap composition of Example 29 was produced by the process described below.

TABLE 21

| Compounded ingredients | Example 29 (weight %) |
|---|---|
| Lauric acid | 5.5 |
| Myristic acid | 11 |
| Palmitic acid | 4 |
| Stearic acid | 5 |
| Oleic acid | 3 |
| 48% Aqueous sodium hydroxide | 7.5 |
| 48% Aqueous potassium hydroxide | 2.7 |
| Glycerin | 7 |
| 70% Sorbitol | 7 |
| Polyoxypropylene (4) glyceryl ether | 8 |
| EDTA-3Na dihydrate | 0.1 |
| Sugar | 10 |
| Lauroylimidazolinium betaine | 6 |
| Polyoxyethylene alkyl-modified dimethylsilicone | 10 |
| Fragrance | 0.8 |
| Red No. 201 (Lithol rubine B) | 0.0001 |
| Plantain extract | 0.05 |
| Ion exchange water | the rest |

Specifically, at a temperature of 65 to 75° C., lauric acid, myristic acid, palmitic acid, stearic acid and oleic acid were dissolved together with glycerin, 70% sorbitol and polyoxypropylene(4) glyceryl ether. This solution was neutralized by addition of 48% aqueous sodium hydroxide and 48% aqueous potassium hydroxide. Fed into this mixture was a solution in which EDTA-3Na dihydrate was dissolved in some of the ion exchange water. Further, at a temperature of 75 to 85° C., sugar, lauroylimidazolinium betaine, polyoxyethylene alkyl-modified dimethylsilicone, the remaining ion exchange water, fragrance, Red No. 201 (lithol rubine B) and plantain extract were added and uniformly dissolved. This mixture was poured into a PET pipe (50 mm in diameter, 40 mm in height) which was equipped with a rubber stopper at the bottom and in which an elastomer figurine was positioned in the middle. In this pipe, the mixture was cooled at a room temperature for solidification. Thereafter, the rubber stopper was removed and the solid product was taken out of the pipe. Thus obtained was a 300-gram transparent bar soap composition which contained the figurine inside the solid body.

The transparent bar soap composition of Example 29, obtained without the aging process, had a solidifying point of 57° C. and showed advantageous properties in transparency and hardness. Besides, this soap composition did not deteriorate in its surface condition and appearance (i.e. no melting and discoloration), even after the long-term storage in the severe environmental condition at 45° C. Further, the soap composition did not sweat under the hot and humid conditions, nor did its surface turn cloudy in the course of use. Furthermore, good transparency ensured clear recognition of the enclosed figurine, thereby giving a novel appearance to the bar soap composition.

In conclusion, the transparent bar soap composition of the present invention exhibits the following effects. For one, the transparent bar soap composition is obtainable without the aging process which is essential in the known technologies. As a result, a great quantity of transparent bar soap products can be quickly put on the market in an economical manner.

For another, the transparent bar soap composition of the present invention is excellent in terms of transparency, hardness and storage stability. Besides, even when the soap composition is stored for a long period under severe environmental conditions, its surface does not suffer from deterioration (e.g. melting or discoloration) or sweating. Further, in the course of use, this soap composition does not turn cloudy at the surface. Such properties are equivalent or superior to those of conventional transparent bar soap compositions manufactured through the aging process. Consequently, the transparent bar soap composition of the present invention can be used effectively, with a high product value.

In particular, these effects are manifested more effectively under the condition where the content of the sodium salt of a fatty acid or that of the mixed sodium/potassium salt of a fatty acid is from 20 to 40% by weight; the content of the amphoteric surfactant is from 2 to 10% by weight; the content of the nonionic surfactant is from 2 to 15% by weight; and the content of the glycerin derivative is from 1 to 10% by weight. Alternatively, the molar ratio of sodium to potassium in the mixed sodium/potassium salt of a fatty acid maybe 10/0 to 7/3, or the glycerin derivative may be of a certain kind.

This application is based on application Nos. 2000-392137 and 2001-280961 filed in Japan, the entire content of which is incorporated hereinto by reference.

What is claimed is:

1. A transparent bar soap composition comprising:

a sodium salt of a fatty acid, or a mixed sodium/potassium salt of a fatty acid;

at least one amphoteric surfactant selected from the group consisting of compounds represented by following formulas (A) to (C),

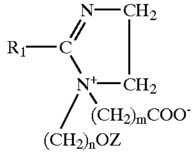

(A)

wherein $R_1$ represents an alkyl group having 7 to 21 carbon atoms or an alkenyl group having 7 to 21 carbon atoms, n and m independently represent an interger from 1 to 3, and Z represents a hydrogen atom or $(CH_2)_pCOOY$, wherein p represents an interger from 1 to 3, and Y represents an alkali metal, an alkaline earth metal or an organic amine, (B)

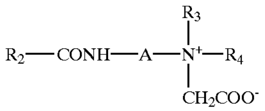

wherein $R_2$ represents an alkyl group having 7 to 21 carbon atoms or an alkenyl group having 7 to 21 carbon atoms, $R_3$ and $R_4$ independently represent a lower alkyl group, and A represents a lower alkylene group, and (C)

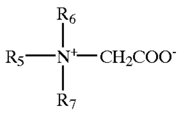

wherein $R_5$ represents an alkyl group having 8 to 22 carbon atoms or an alkenyl group having 8 to 22 carbon atoms, and $R_6$ and $R_7$ independently represent a lower alkyl group;

a nonionic surfactant; and at least one glycerin derivative.

2. The transparent bar soap composition according to claim 1, which comprises:

20 to 40% by weight of the sodium salt of a fatty acid or the mixed sodium/potassium salt of a fatty acid;

2 to 10% by weight of the amphoteric surfactant;

2 to 15% by weight of the nonionic surfactant; and 1 to 10% by weight of the glycerin derivative.

3. The transparent bar soap composition according to claim 1, wherein the molar ratio of sodium to potassium in the mixed sodium/potassium salt of a fatty acid is 10/0 to 7/3.

4. The transparent bar soap composition according to claim 1, wherein the glycerin derivative is at least one member selected from the group consisting of polyoxypropylene glyceryl ether, polyoxypropylene diglyceryl ether, polyoxypropylene polyglyceryl ether, polyoxyethylene polyoxypropylene glyceryl ether, polyoxyethylene polyoxypropylene diglyceryl ether, and polyoxyethylene polyoxypropylene polyglyceryl ether.

* * * * *

UNITED STATES PATENT AND TRADEMARK OFFICE
CERTIFICATE OF CORRECTION

PATENT NO. : 6,656,893 B2
DATED : December 2, 2003
INVENTOR(S) : Saito et al.

It is certified that error appears in the above-identified patent and that said Letters Patent is hereby corrected as shown below:

Column 2,
Lines 40 and 42, please change "interger" to -- integer --

Column 22,
Line 66, please change "interger" to -- integer --, and

Column 23,
Line 1, please change "interger" to -- integer --

Signed and Sealed this

Twenty-second Day of June, 2004

JON W. DUDAS
*Acting Director of the United States Patent and Trademark Office*